US007082631B2

(12) United States Patent  
Czop

(10) Patent No.: US 7,082,631 B2
(45) Date of Patent: Aug. 1, 2006

(54) IMAGING TABLE PROTECTIVE COVER

(75) Inventor: Michael W. Czop, Fenton, MI (US)

(73) Assignee: Contour Fabricators, Inc., Fenton, MI (US)

( * ) Notice: Subject to any disclaimer, the term of this patent is extended or adjusted under 35 U.S.C. 154(b) by 0 days.

(21) Appl. No.: 10/896,704

(22) Filed: Jul. 22, 2004

(65) Prior Publication Data

US 2006/0016004 A1    Jan. 26, 2006

(51) Int. Cl.
    *A47G 9/04*    (2006.01)
(52) U.S. Cl. .................... 5/484; 5/411; 5/601; 378/209
(58) Field of Classification Search .............. 5/625, 5/626, 699, 484, 502, 601, 628, 81.1, 81.1 HS; 378/209; 108/90
    See application file for complete search history.

(56) References Cited

U.S. PATENT DOCUMENTS

| 3,861,666 | A | * | 1/1975 | Nishiyama et al. ............ 5/601 |
| 4,484,571 | A | | 11/1984 | Velazquez |
| 4,910,819 | A | | 3/1990 | Brown |
| 4,991,242 | A | | 2/1991 | Brown |
| 5,070,520 | A | | 12/1991 | Brown |
| 5,121,514 | A | * | 6/1992 | Rosane ............................ 5/628 |
| 5,189,746 | A | * | 3/1993 | Horie .............................. 5/627 |
| 5,396,672 | A | | 3/1995 | Brown |
| 5,860,174 | A | * | 1/1999 | Failor ...................... 5/81.1 HS |
| 5,983,426 | A | | 11/1999 | Vanek et al. |
| 6,128,796 | A | * | 10/2000 | McCormick et al. ........... 5/626 |
| 6,510,595 | B1 | | 1/2003 | Matsushima et al. |

\* cited by examiner

*Primary Examiner*—Michael Trettel
(74) *Attorney, Agent, or Firm*—John K. McCulloch

(57) ABSTRACT

A cover and patient restraint for use with a radiologic imaging table having an upper surface on which a patient may lie, the cover having a central section corresponding generally to the length and width of the patient supporting surface of the table and a width substantially greater than that of the supporting surface so the opposite sides of the cover form flaps which extend beyond and depend from the upper surface of the table to prevent the collection on the table surface of liquids. The cover includes a pad of cushioning material inboard of the flaps to enhance the comfort of a patient lying on the cover. Restraining straps are coupled to anchor strips extending longitudinally of the cover adjacent opposite sides of the pad so as to enable the straps to be placed in overlying relation to the patient in any selected one of a large number of adjusted positions. The cover is encapsulated in a pliable, washable, radiologic inert coating.

20 Claims, 4 Drawing Sheets

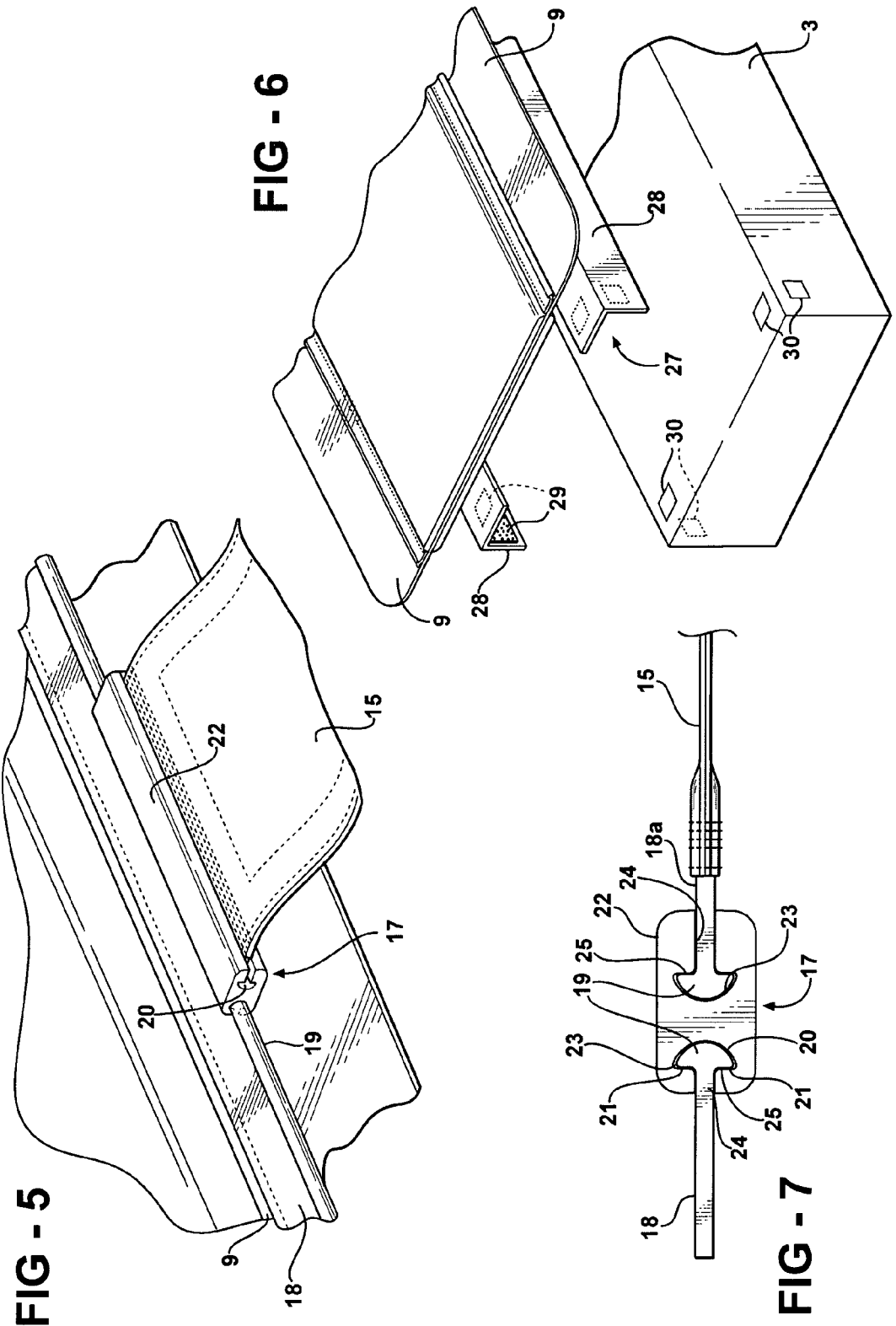

IMAGING TABLE PROTECTIVE COVER

This invention relates to a protective cover for use in connection with a radiologic imaging table.

BACKGROUND OF THE INVENTION

Radiologic imaging is used extensively for diagnostic procedures and the monitoring of patients. The imaging apparatus conventionally includes a table or other support on which a patient may lie for exposure to imaging apparatus having cooperable components positioned below and above the patient. The imaging components carried by the patient support are particularly vulnerable to fluids originating from a patient or spilled by technicians. Such fluids have a tendency to collect atop the patient support, or even seep into the support, resulting in contamination of the surface of the support and interference with the operation of the imaging apparatus. Further, the collection of fluids requires careful cleaning which often consumes so much time that the imaging apparatus cannot be used when needed.

The problems associated with the collection of fluids atop patient supports have been considered heretofore and solutions proposed, but not all of the proposed solutions have been satisfactory for a number of reasons. For example, some protective covers proposed heretofore are exceedingly complicated in construction, thereby delaying the application and removal of such covers to and from a patient's support. If such a cover is one which cannot be cleaned and reused, the cost of utilization of such covers is unacceptably high.

In some cases a patient who is unconscious or incapable of controlling his movements must be restrained so as to avoid injuring himself or rendering the imaging procedures ineffective. In some instances, however, fixed restraints such as straps cannot be used if they overlie or bear against a traumatized portion of the patient's body. However, not all restraining straps are sufficiently adjustable relative to the patient to provide the necessary restraint at an appropriate position of the patient's body.

A principal object of the invention is to provide a protective cover and patient restraint construction that will overcome the disadvantages referred to above.

SUMMARY OF THE INVENTION

Apparatus constructed in accordance with the invention comprises a sheet formed of pliable, waterproof material which is adapted to overlie the patient supporting surface of a table or other support in which components of imaging apparatus are housed. The sheet has a length corresponding substantially to that of the support surface and a width greater than that of the support surface so that when the sheet is applied to the surface of the table a central section of the sheet rests upon the patient supporting surface of the table and is flanked by flaps which extend beyond and depend from the table surface. Preferably, the center section of the cover includes a pad of cushioning material so as to enhance the comfort of the patient. Preferably, the entire sheet, including the flaps, is encapsulated in a coating of pliable, durable, easily cleanable material so as to facilitate cleaning of the cover between successive uses thereof.

Restraining straps are provided to restrain movements of a patient lying on the cover. Each strap is coupled to the cover in such manner as to enable the strap to be moved longitudinally of the cover to any selected position of adjustment. The coupling is one which not only permits such longitudinal adjustment, but also is quickly attachable to and detachable from the cover. The coupling apparatus is wholly external of the encapsulating coating.

The flaps and the adjacent sides of the patient supporting table preferably are equipped with separable retainers for separably securing the flaps in depending relation to the table surface.

The materials from which the apparatus is formed are inert insofar as the radiologic imaging apparatus is concerned, thereby avoiding any interference with the imaging procedures.

THE DRAWINGS

The preferred embodiment of the invention is illustrated in the accompanying drawings wherein:

FIG. 5 is an enlarged, fragmentary, isometric view of apparatus for coupling a restraining strap to the cover;

FIG. 6 is a fragmentary, isometric, exploded view illustrating one manner in which the cover may be separably secured to the upper part of a patient support;

FIG. 7 is an enlarged end elevational view of the strap coupling apparatus.

THE PREFERRED EMBODIMENT

Figure 1:
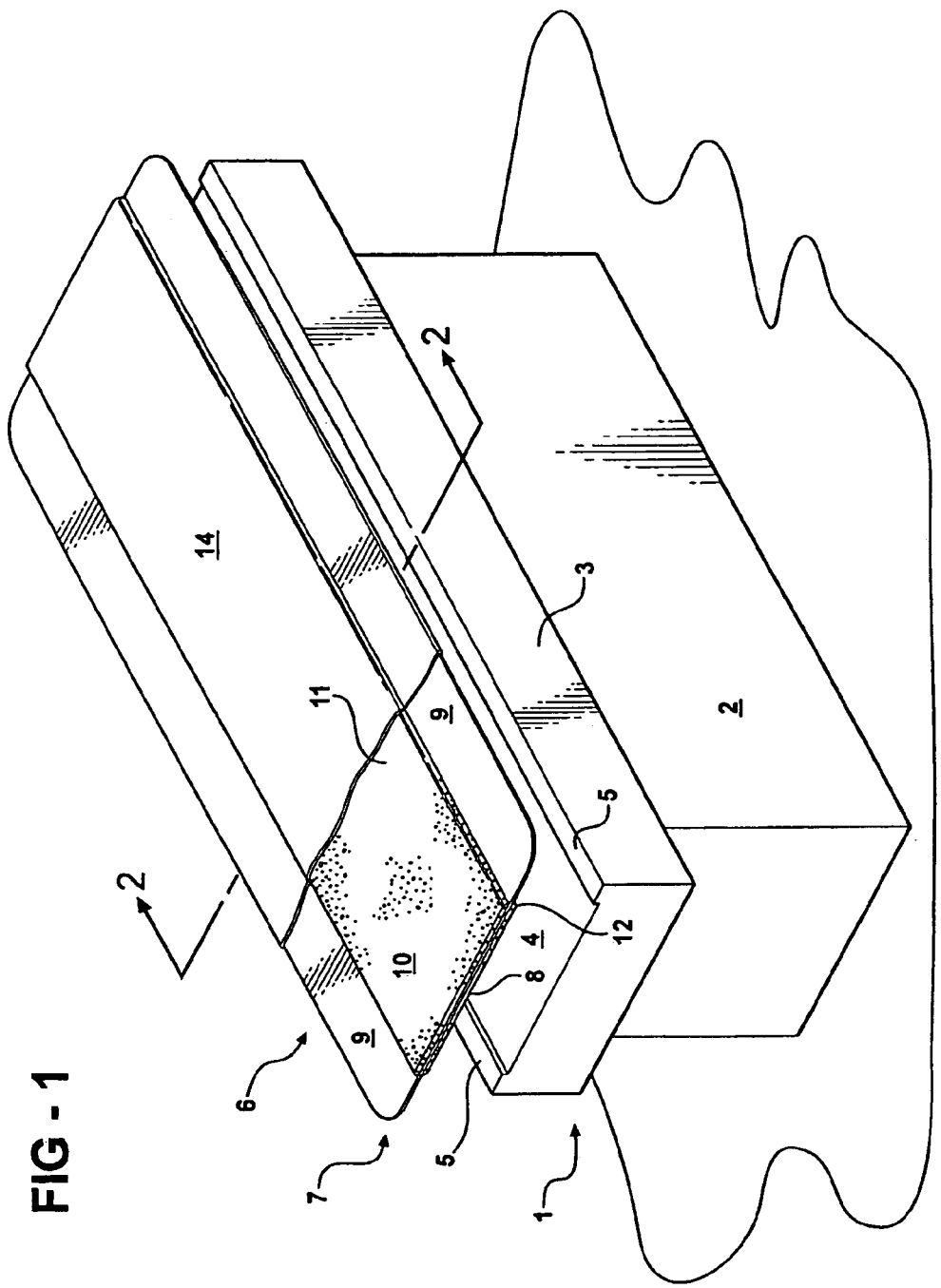
FIG. 1 is an isometric view, with parts broken away, illustrating a cover adapted to be applied to an imaging table and in overlying relation therewith.
Figure 2:
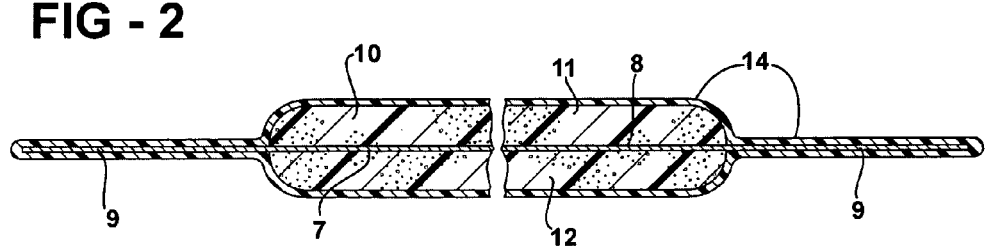
FIG. 2 is a greatly enlarged sectional view taken on the line 2—2 of FIG. 1.
Figure 3:
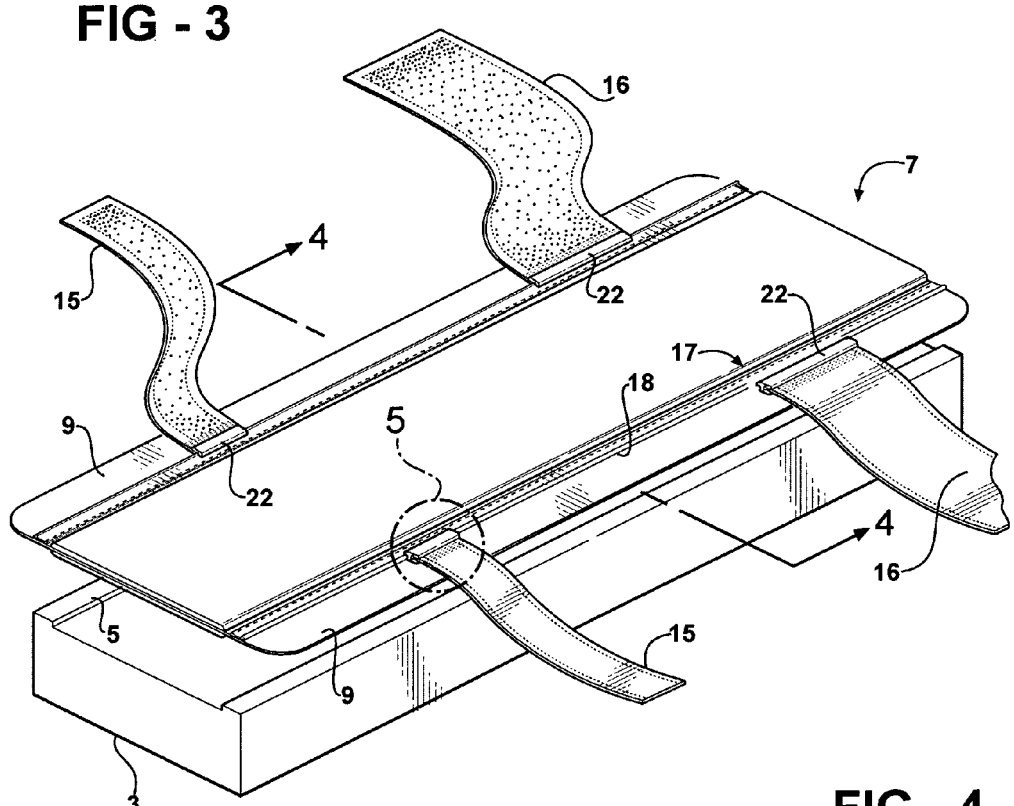
FIG. 3 is a view similar to FIG. 1, but omitting the external coating and illustrating patient restraining straps coupled to the cover.
Figure 4:
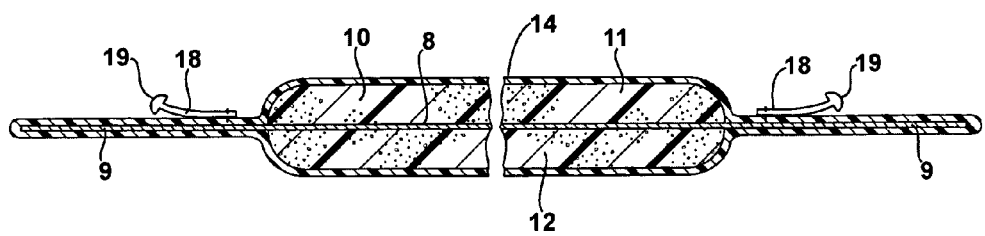
FIG. 4 is an enlarged sectional view taken on the line 4—4 of FIG. 3.
Figure 8:
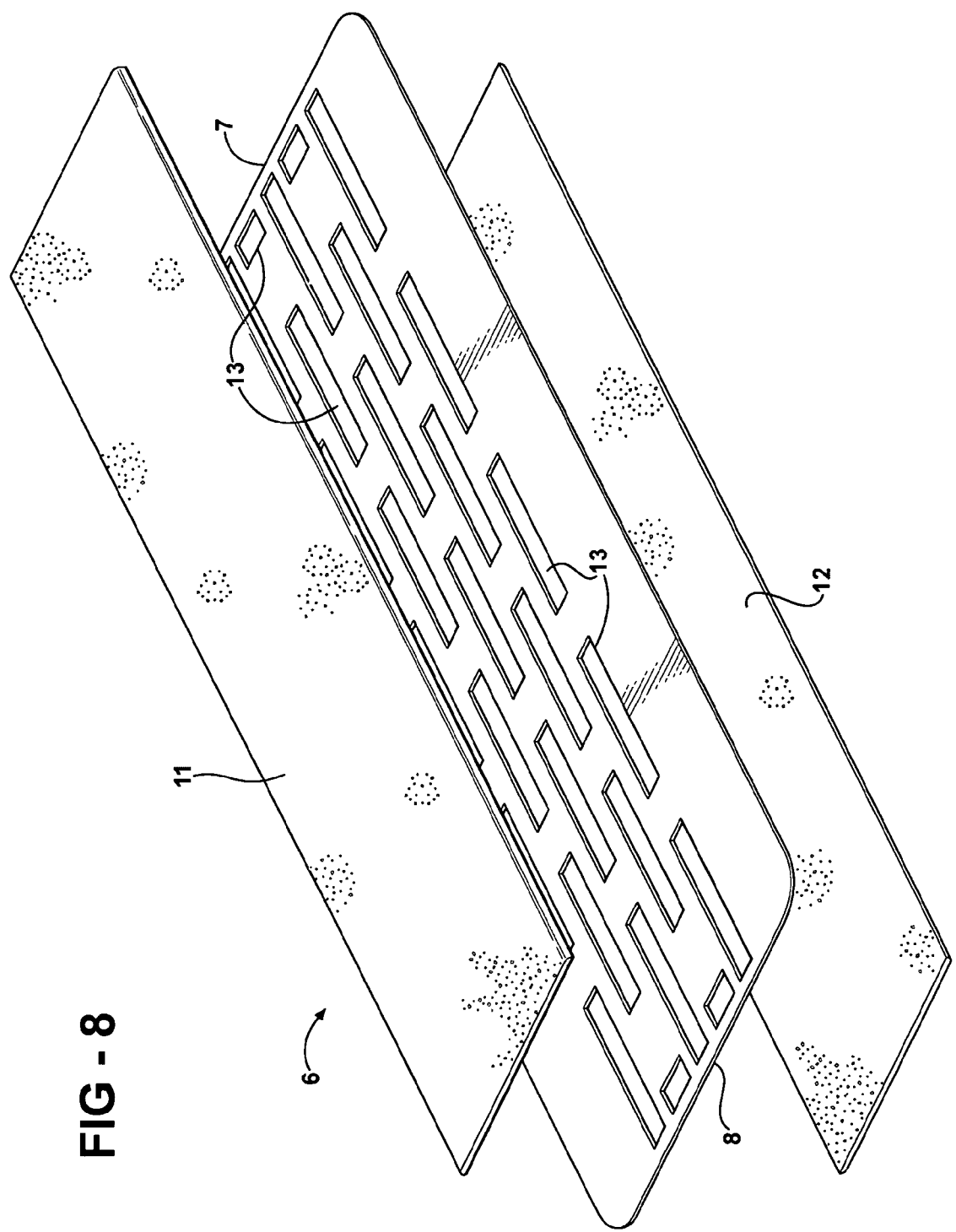
FIG. 8 is an enlarged, isometric, exploded view of a cover and a pad prior to the pad's being adhered to a cover.

Apparatus constructed in accordance with the invention is adapted for use with a support table 1 having a base 2 supporting a top 3 having an upper surface 4 flanked by longitudinally extending rails 5. The base 2, or the top 3, or both, include radiologic imaging components (not shown) which cooperate with other components contained in an overhead support (not shown) for producing diagnostic images of a patient lying atop the table. The rails 5 help define the area to be occupied by the patient during the diagnostic process. However, the rails, if used, tend to enable fluids to collect on the upper surface of the table, thereby making cleaning of the table between uses more complicated and, perhaps, enabling such fluids to seep into the interior of the support.

The apparatus comprises a cover 6 formed from a sheet 7 of waterproof, pliable material such as polyvinyl chloride which is inert with respect to the imaging apparatus. The sheet 7 has a center section 8 having a length corresponding substantially to the length of the table top 3 and a width substantially greater than that of the table top so that, when the center section overlies the surface 4, the opposite sides of the sheet extend beyond the table top 3 and form flaps 9 which, because of the pliability of the sheet material, may depend and occupy positions adjacent the upper sides of the table.

Secured to the center section 8 of the sheet 7 inboard of the flaps 9 is a pad 10 formed of cushioning material which is inert to the imaging apparatus. The material could be an open cell foam, such as polyurethane, or a closed cell ethylenevinyl acetate foam. The pad 10 may be cemented by any suitable adhesive to one side only of the sheet 7, but it is preferred to use two identical halves 11 and 12 between which the center section 8 of the sheet is sandwiched. This construction is preferred because it enables openings 13 to be provided in the center section 8 of the sheet, thereby permitting each half to be adhered not only to the sheet itself, but to each other via the openings 13. This construction provides an extremely secure attachment of the pad to the sheet.

Preferably, but not necessarily, the assembly of the sheet 7 and the pad 10 is encapsulated by a pliable, waterproof coating 14 which forms the exterior surface of the cover. The material from which the coating is formed is a suitable liquid such as a commercially available vinyl emulsion or solution containing known percentages of polymeric resins, other materials, and water or solvents. The coating may be applied in liquid form by dipping, brushing, or spraying, followed by curing of the coating in an oven or at ambient temperature. A suitable coating is available from Contour Fabricators, Inc. of Fenton, Mich., under the trademark SCANCOAT. However, any coating which has the desired characteristics of being waterproof, washable, and durable may be used, as long as the material of the coating enhances X-ray radiolucency and diminishes computerized tomography artifacting.

In some of the drawing figures the coating is shown with an exaggerated thickness, whereas in others the coating is omitted for purposes of clarity.

The apparatus preferably includes a plurality of pairs of restraining straps 15 and 16. The two straps 15 are identical to one another and the two straps 16 are identical to one another, and the pairs of straps 15 and 16 are the same except for width. Each of the straps is formed from a radiologic inert material such as rayon, nylon, or other strong, flexible material and each strap is coupled at one of its ends to an associated flap 9 of the cover 6 adjacent the pad 10. The coupling means is designated generally by the reference character 17 in FIGS. 5 and 7 and, in each instance, includes an anchor strip 18 stitched or otherwise suitably secured to a flap 9 adjacent and longitudinally parallel to the pad 10. The anchor strip 18 may be secured to the flap 9 by stitching, heat sealing or welding, adhesively, or in any other conventional manner. Preferably, the anchor strip 18 is external of the coating 14 on the flaps 9 and is formed from radiologic inert material such as a polyester available under the trademark MYLAR and having sufficient stiffness to be form stable. At its free end the anchor strip 18 terminates in an integral enlargement or bead 19 of substantially semispherical configuration in cross section. The outer surface 20 (FIGS. 7) of the enlargement 19 is arcuate, whereas the inner surface is flat and forms a pair of coplanar shoulders 21 flanking the strip 18.

Each of the straps 15, 16 has one end stitched or otherwise suitably secured at one end to an anchor strip 18a which is identical to the strip 18 and has a corresponding semihemispherical enlargement or bead 19. Each of the anchor strips 18, 18a is adapted for removable and slideable mounting in a coupling body member 22 having a pair of spaced, semispherical channels 23 therein, each of which communicates with an access slot 24 of such width as slideably to accommodate the associated strip 18, 18a. Each channel 23 has flanges 25 on opposite sides of the slot, and the inner surfaces of such flanges form coplanar stops against which the planar shoulders 21 of the beads 19 bear.

From the foregoing description it will be clear that the coupling means by which each strap is secured to the cover includes two anchor strips, two enlargements or beads, and one coupling body member having a pair of channels therein.

The construction and arrangement of the coupling means are such that the body member 22 can be secured to the strip 18 by fitting the enlargement 19 at one end of the strip into one of the channels 23 and by fitting the enlargement 19 at the free end of the strip 18a into the other channel 23 from one end of the body member 22. The body member then may be slid longitudinally of the straps 18, 18a to any desired position along the length of the cover.

The planar configuration of the shoulders 21 and the flanges 25 cooperate to retain the enlargements in the channels more securely than if the surfaces of the enlargements confronting the flanges were rounded. This is because the presence of rounded surfaces on the enlargements would enable the latter to act as cams and spread the flanges 25.

Each of the straps 15, 16 is of such length as to overlie the pad and at least a portion of a patient lying on the pad. The two free ends of each pair of straps may be fastened to one another by suitable fastening means, such as confronting hook and pile sections 26 like that sold by Velcro, Inc. under the trademark VELCRO. However, other separable fasteners may be used. For example, the straps could be provided with radiologic inert buckles, grippers, or releasable contact adhesives so as to provide a secure, but separable, means for fixing the straps in overlying relation to a patient lying on the cover.

If desired, the cover may be releasably fastened to the table 3 in any one of a number of different ways. For example, a pair of supports 27 may be stitched, adhesively, or otherwise secured to the lower surfaces of the flaps 9 and each support may be provided with appropriately placed VELCRO or other fasteners 29 for cooperation with correspondingly placed VELCRO fasteners 30 secured to the table 3. The support 28 is shown in FIG. 6 as being right angular in configuration, but it should be understood that such supports are formed of pliable materials like those referred to earlier so that they do not interfere with the flaps 9 assuming their depending positions. By securing the cover to the table the restraining force that can be applied via the straps 15, 16 to a patient is enhanced.

The disclosed embodiment is representative of a presently preferred form of the invention, but is intended to be illustrative rather than definitive thereof. The invention is defined in the claims.

I claim:

1. A combined protective cover, cushion, and restraint construction adapted for use with an imaging table having an upper surface of selected length and width, said construction comprising a sheet of pliable, waterproof material having a width greater than that of said surface so that when said sheet is placed atop said surface opposite sides of said sheet may extend beyond said surface and form depending flaps; a pad of cushioning material having a width corresponding substantially to that of said surface and secured to said sheet at a position inboard of said flaps; at least one flexible restraining strap; first anchor means secured to at least one of said flaps adjacent one side of said pad; second anchor means secured to one end of said strap; and coupling means interposed between said first and second anchor means and coupling said first and second anchor means for sliding movements relative to one another and to said sheet, said strap being of such length as to overlie said pad and at least a portion of a person lying thereon.

2. The construction according to claim 1 including a second strap corresponding to said one strap, first and second anchor means corresponding to the first and second anchor means referred to in claim 1 secured to the other of said flaps and to one end of said second strap, and second coupling means corresponding to the coupling means referred to in claim 1 for securing said second strap to said sheet at the opposite side thereof, said second strap being of such length as to overlie said cushion and at least a portion of a person lying thereon.

3. The construction according to claim 2 including means for separably securing said first and second straps together.

4. The construction according to claim 1 wherein said sheet passes through said cushion so that portions of said pad are on opposite sides of said sheet.

5. The construction according to claim 4 wherein that portion of said sheet which passes through said pad has openings therein.

6. The construction according to claim 1 including a coating of pliable, waterproof material encapsulating said sheet and said cushion.

7. The construction according to claim 6 wherein said first and second anchor means are external of said coating.

8. The construction according to claim 1 wherein each said anchor means comprises a strip of material extending longitudinally of said one flap and wherein said coupling means comprises a body having a channel therein extending longitudinally of said strip, said channel having a substantially semispherical cross section and an access slot in communication with said channel.

9. The construction according to claim 8 wherein said anchor means comprises a semihemispherical projection at one end of said strip, said projection being slideably accommodated in said channel, said strip being slideably accommodated in said slot, and means securing said strip to said strap.

10. A combined protective cover, cushion, and restraint construction adapted for use with an imaging table having an upper surface of selected length and width, said construction comprising a sheet of pliable, waterproof material of selected length and a width greater than that of said surface so that when said sheet is placed atop said surface a central section of said sheet overlies said surface and opposite sides of said sheet may extend beyond said central section and forms flaps which may depend from said central section; a pad of cushioning material secured to said central section of said sheet and having a width corresponding substantially to that of said central section; at least one restraining strap; first anchor means secured to said sheet adjacent said central section; and second anchor means secured to one end of said strap cooperable with said first anchor means for coupling said first and second anchor means, said strap being of such length as to be able to overlie said pad and a patient lying atop said pad.

11. The construction according to claim 10 wherein said first anchor means comprises a strip secured along one side thereof to said sheet and extending longitudinally of said sheet, said strip having an opposite side terminating in a bead extending the full length of said strip.

12. The construction according to claim 11 wherein said coupling means comprises a body member having a channel therein of such size as to accommodate said bead, said body member having a slot in communication with said channel and in which said strip is accommodated.

13. The construction according to claim 12 wherein said body member has a second channel therein and a second slot in communication with said second channel, said strap having at said one end thereof a bead of such size and shape as to be accommodated in said second channel, said one end of said strip being of such thickness as to be accommodated in said second slot.

14. The construction according to claim 13 wherein said pad and said sheet, including said flaps, are encapsulated within a waterproof coating.

15. The construction according to claim 14 wherein said anchor means is external of said cover.

16. A protective cover construction adapted for use with an imaging table having an upper surface of selected length and width, said construction comprising a sheet of pliable material having a width greater than that of said surface so that when said sheet is placed atop said surface opposite sides of said sheet may extend beyond said surface and form depending flaps; a pad of cushioning material having a width corresponding substantially to that of said surface and secured to said sheet at a position inboard of said flaps; and a waterproof, washable coating encapsulating said sheet and said flaps, said sheet passing through said pad thereby dividing said pad into separate parts on opposite sides of said sheet.

17. The construction according to claim 16 wherein each of said parts of said pad is adhered to said sheet.

18. The construction according to claim 17 wherein said sheet has openings therein thereby enabling areas of said pad overlying said openings to be adhered to each other.

19. A combined protective cover, cushion, and restraint construction adapted for use with an imaging table having an upper support surface of selected length and width, said construction comprising a sheet of pliable, waterproof material having a length corresponding substantially to that of said surface and a width greater than that of said surface so that when said sheet is placed atop said surface opposite sides of said sheet extend beyond said surface and form depending flaps; a pad inboard of said flaps formed of cushioning material and through which said sheet passes so as to form two halves sandwiching said sheet therebetween; means adhering each of said halves to said sheet; a pair of restraining straps; first strap retaining means secured to said sheet adjacent one side of said pad and extending longitudinally of said sheet; second strap retaining means secured to said sheet adjacent the opposite side of said pad and extending parallel to said first retaining means; third strap retaining means secured to one end of one of said straps; fourth strap retaining means secured to one end of the other of said straps, said first, second, third, and fourth retaining means corresponding to one another; and a pair of coupling body members one of which couples one of said straps to one of the retaining means on said sheet and the other of which couples the other of said straps to the other retaining means on said sheet, each said coupling body member being slideably coupled to the associated retaining means.

20. A combined protective cover and restraint construction adapted for use with an imaging table having an upper surface of selected length and width, said construction comprising a sheet of pliable, waterproof material having a width greater than that of said surface so that when said sheet is placed atop said surface a central section of said sheet may overlie said surface and opposite sides of said sheet may extend beyond said surface and form flaps; at least one flexible restraining strap; first anchor means secured to at least one of said flaps adjacent one side of said central section; second anchor means secured to one end of said strap; and coupling means interposed between said first and second anchor means and coupling said first and second anchor means for sliding movements relative to one another and to said sheet, said strap being of such length as to overlie said central section and at least a portion of a person lying thereon.

* * * * *

UNITED STATES PATENT AND TRADEMARK OFFICE
CERTIFICATE OF CORRECTION

| | |
|---|---|
| PATENT NO. | : 7,082,631 B2 |
| APPLICATION NO. | : 10/896704 |
| DATED | : August 1, 2006 |
| INVENTOR(S) | : Michael W. Czop |

It is certified that error appears in the above-identified patent and that said Letters Patent is hereby corrected as shown below:

Column 5, each of lines 7, 12, and 19, change

"cushion" to -- pad --.

Signed and Sealed this

Twenty-first Day of November, 2006

JON W. DUDAS
*Director of the United States Patent and Trademark Office*